Figure 1:
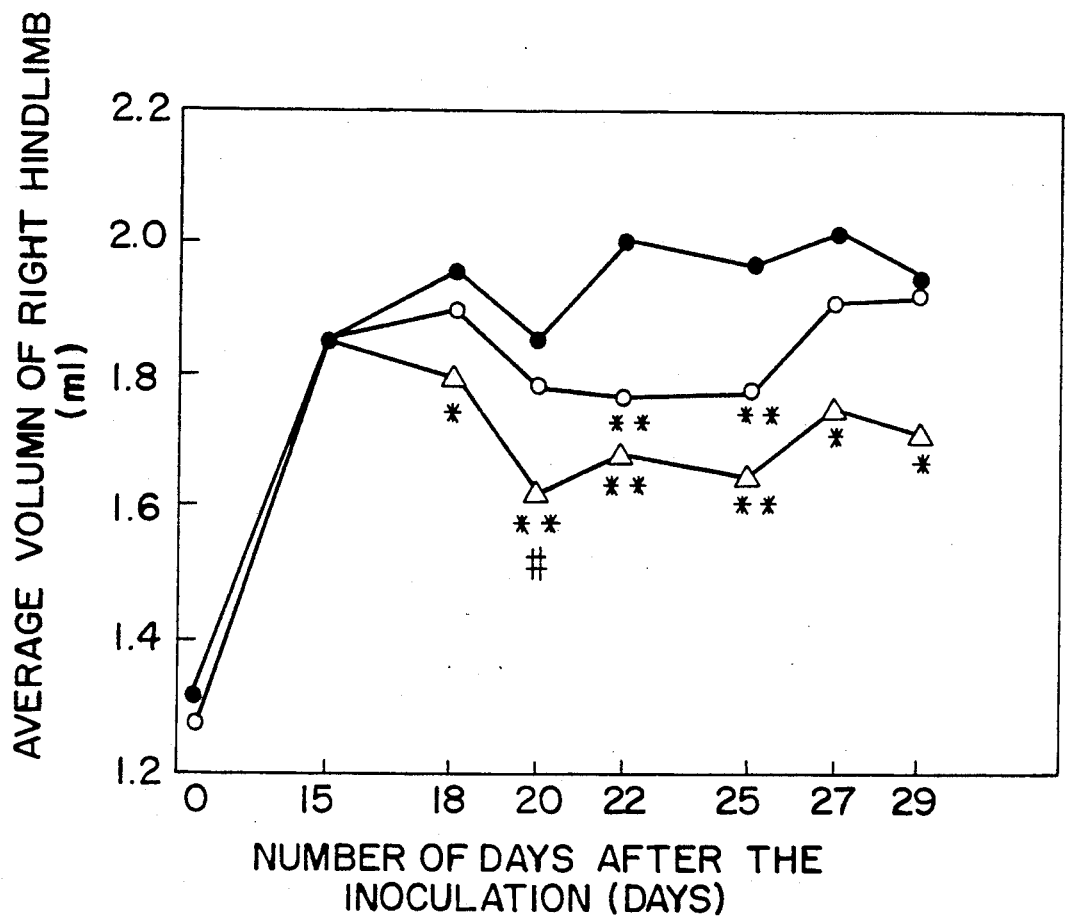

United States Patent [19]

Mizushima et al.

[11] Patent Number: 5,015,746

[45] Date of Patent: May 14, 1991

[54] 11β,17α,21-TRIHYDROXY-1,4-PREGNADIENE-3,20-DIONE 21-[(E,E)-3,7,11-TRIMETHYL-2,6,10-DODECATRIENOATE]

[75] Inventors: Yutaka Mizushima, Tokyo; Keiko Hoshi, Yokohama; Rie Igarashi, Kawasaki; Hirofusa Ajioka, Tokushima; Noriyuki Yamamoto; Masahito Komuro, both of Tokushima; Koichi Kanehira, Kurashiki; Masayuki Inoue, Kurashiki; Takashi Nishida, Kurashiki; Manzo Shiono, Okayama; Michio Terasawa, Nakatsu; Kenzo Arizono, Nakatsu, all of Japan

[73] Assignee: Kuraray Co., Ltd., Okayama, Japan

[21] Appl. No.: 299,681

[22] Filed: Jan. 23, 1989

[30] Foreign Application Priority Data

Mar. 9, 1988 [JP] Japan ................. 63-57135
Mar. 31, 1988 [JP] Japan ................. 63-80542

[51] Int. Cl.$^5$ ............................................. A61K 31/56
[52] U.S. Cl. ..................................... 552/569; 552/559
[58] Field of Search ............... 260/397.45; 514/179; 552/569

[56] References Cited

U.S. PATENT DOCUMENTS 3,488,421 1/1970 Casadio ........................... 514/179

FOREIGN PATENT DOCUMENTS 229824 10/1986 Japan.
1187395 4/1970 United Kingdom.

OTHER PUBLICATIONS

Chemical Abstracts, vol. 110, #33848a; Mizushima et al.
Chemical Abstracts, vol. 105 (1986) #203378p; Mizushima et al.
Chemical Abstracts; vol. 71 (1969) #61678q; Istituto DeAngeli.
Medicina, 22(7), p. 1174 (1985).
3rd Japan DDS Research Society Conference Program Preliminary Draft Report, p. 52 (1987).
8th Japanese Society of Inflammation Program Preliminary Draft Report, p. 90 (1987).
Mebio, 4(8), p. 78 (1987).
3rd Transdermal Therapeutic System Symposium Program, p. 4 (1987).
108th Pharmaceutical Society of Japan, p. 580 (1988).

*Primary Examiner*—Stanley J. Friedman
*Assistant Examiner*—Theodore J. Criares
*Attorney, Agent, or Firm*—Wenderoth, Lind & Ponack

[57] ABSTRACT

11β,17α,21-Trihydroxy-1,4-pregnadiene-3,20-dione 21-[(E,E)-3,7,11-trimethyl-2,6,10-dodecatrienoate] of the formula an antiinflammatory composition thereof and a method for the production thereof.

11β,17α,21-Trihydroxy-1,4-pregnadiene-3,20-dione 21-[(E,E)-3,7,11-trimethyl-2,6,10-dodecatrienoate] of the present invention exhibits remarkably excellent antiinflammatory action and besides, displays reduced side effects and can be produced in high selectivity and good yield and conveniently.

1 Claim, 2 Drawing Sheets

11β,17α,21-TRIHYDROXY-1,4-PREGNADIENE-3,20-DIONE 21-[(E,E)-3,7,11-TRIMETHYL-2,6,10-DODECATRIENOATE]

This invention relates to a novel compound in which prednisolone (11β,17α,21-trihydroxy-1,4-pregnadiene-3,20-dione) is modified by a terpene and to an antiinflammatory composition containing the same, and a method for the production of the same.

Hitherto, it has been known that in the esters of pregnane derivatives such as cortisone, hydrocortisone, prednisone, prednisolone, dexamethasone, triamcinolone, paramethasone, betamethasone and the like which can be obtained by esterifying the corresponding pregnane derivatives possessing antiinflammatory actions at the 21-position at which hydroxyl group exists with the use of the reactive derivatives such as acid halides and acid anhydrides of terpene acids such as geranic acid, homogeranic acid, geranylacetic acid, citronellic acid, farnesic acid, homofarnesic acid and farnesylacetic acid, the side effects which the pregnane derivatives as the starting compounds display are reduced, and the activities are generally increased as compared with the pregnane derivatives when applied externally (See U.S. Pat. No. 3,488,421).

A part of the present inventors reported that prednisolone 21-farnesylate[11β,17α,21-trihydroxy-1,4-pregnadiene-3,20-dione 21-(3,7,11-trimethyl-2,6,10-dodecatrienoate)] which had not been specifically described in said U.S. Patent had an inhibitory action against thymidine incorporation by human lymphocytes which undertook blastogenic transformation by phytohemagglutinin [See Medicina vol. 22. No. 7 (1985) pp. 1174–1175 and Mebio vol. 4. No. 8 (1987) pp. 78–92] and that prednisolone 21-farnesylate reached the deep site by frequent applications in animal inflammatory models [The 8th Japan Inflammation Society Conference Program Preliminary Draft Report (Published on June 30, 1987), p. 90, 27 and The 3rd Japan DDS Research Society Conference Program Preliminary Draft Report p. 52. PS-16 (The 3rd Japan DDS Research Society Conference held on July 11, 1987).

The present inventors found that prednisolone 21-farnesylate has a higher antiinflammatory action than prednisolone and rarely exhibits such side effects as atrophy of thymus gland which are found with prednisolone. It is more desirable to provide terpene-modified compounds of prednisolone which exhibit more excellent antiinflammatory action in respect of the treatment of inflammations.

Thus, it is one of the objects of the present invention to provide a novel terpene-modified compound of prednisolone which not only exhibits a higher antiinflammatory activity and fewer side effects but also is more excellent in durability of antiinflammatory action than prednisolone. It is another object of the present invention to provide an antiinflammatory composition containing said terpene-modified compound.

In the meantime, Prednisolone 21-farnesylate has four geometrical isomers since it has geometrical isomerism on the double bonds at the 2 position and at the 6-position of the 3,7,11-trimethyl-2,6,10-dodecatrienoyl group. However, from the above-mentioned reports concerning prednisolone 21-farnesylate, it is not evident whether said prednisolone 21-farnesylate is a single geometrical isomer or a mixture of plural geometrical isomers, and the method for the production thereof is neither evident.

When prednisolone 21-farnesylate is used as a medicine such as an antiinflammatory drug, it is desirable that said prednisolone 21-farnesylate is used as a single geometrical isomer from the viewpoint that the quality of the medicine can be constant. Although from this viewpoint, the present inventors studied various methods for the esterification to produce 11β,17α,21-trihydroxy-1,4-pregnadiene-3,20-dione 21-[(E,E)-3,7,11-trimethyl-2,6,10dodecatrienoate] [hereinafter referred to as prednisolone 21-(2E,6E-farnesylate)] which is one of prednisolone 21-farnesylate geometrical isomers from (E,E)-3,7,11-trimethyl-2,6,10-dodecatrienoic acid (hereinafter referred to as 2E,6E-farnesylic acid) which is one of 3,7,11-trimethyl-2,6,10-dodecatrienoic acid geometrical isomers and prednisolone, they found that there were problems such as the problem that in many cases, there was by-produced a large amount of 11β,17α,21-trihydroxy-1,4-pregnadiene-3,20-dione 21-[(Z,E)-3,7,11-trimethyl-2,6,10-dodecatrienoate] [hereinafter referred to as prednisolone 21-(2Z,6E-farnesylate)] which is a geometrical isomer of prednisolone 21-(2E,6E-farnesylate) and the problem that it was difficult to produce prednisolone 21-(2E,6E-farnesylate) with high selectivity and in high yield.

In Angewandte Chemie International Edition in English, vol. 17, No. 7 (1978), pp. 522–524, there is reported that the corresponding esters were obtained by reacting a carboxylic acid such as 1-phenylcyclohexane-1-carboxylic acid, cinnamic acid, malonic acid and so on with an alcohol such as methanol and tert-butyl alcohol in the presence of N,N'-dicyclohexylcarbodiimide and 4-(dimethylamino)pyridine respectively. However, there is not given any report as to the esterification reaction of one of geometrical isomers of carboxylic acids having methylethenylene group such as 2E,6E-farnesylic acid and geometrical isomerism of methyl cinnamate and tert-butyl cinnamate which have been produced by the esterification of cinnamic acid.

Thus, the third object of the present invention is to provide a method for producing prednisolone 21-(2E,6E-farnesylate) which is one of geometrical isomers of prednisolone 21-farnesylate in high selectivity and yield and with ease.

According to the present invention, the above-mentioned objects can be attained by providing prednisolone 21-(2E,6E-farnesylate) represented by the formula

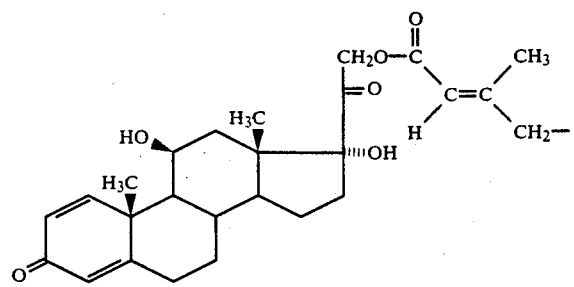

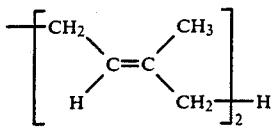

and an antiinflammatory composition containing as the effective ingredient said prednisolone 21-(2E,6E-farnesylate).

Prednisolone 21-(2E,6E-farnesylate) can be produced by reacting prednisolone or a reactive derivative thereof with 2E,6E-farnesylic acid or a reactive derivative thereof. Preferably, the reaction of prednisolone with 2E,6E-farnesylic acid is conducted in the presence of (disubstituted amino)-pyridines and a condensing agent.

Figure 2:
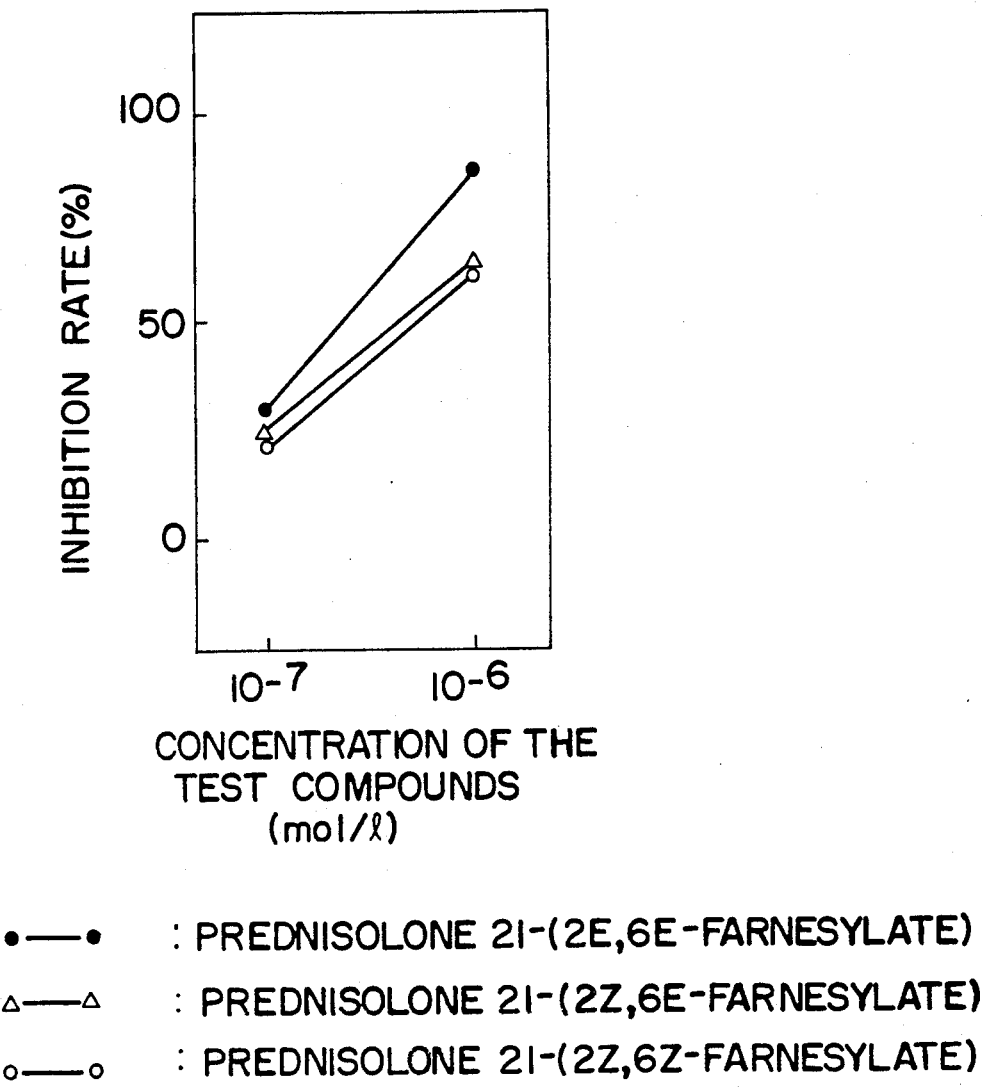

FIG. 1 shows the results of Adjuvant arthritis test in Test Example 2. FIG. 2 shows the results of the tests for the inhibition of thimydine incorporation into human lymphocyte subjected to blast transformation in Test Example 3.

As the reactive derivatives of prednisolone, there may be mentioned halides, alkanesulfonates, arenesulfonates, carboxylates and the like. As the reactive derivatives of 2E,6E-farnesylic acid there may be mentioned lower alkyl esters, acid halides, mixed acid anhydrides, alkali metal salts, silver salts, salts of organic tertiary or quaternary base and the like. The reaction of prednisolone or a reactive derivative thereof with 2E, 6E-farnesylic acid or a reactive derivative thereof can be conducted generally under the conditions of the conventional ester-synthesizing reactions which have been hitherto known. There are described representative examples of said ester-synthesizing reactions below.

Reaction Example a

Reaction of prednisolone with an acid halide of 2E,6E-farnesylic acid.

Prednisolone 21-(2E,6E-farnesylate) can be obtained by reacting prednisolone with an acid halide, preferably acid chloride, of 2E,6E-farnesylic acid in an amount of about 0.5 to 10 equivalent, preferably 0.9 to 2.0 equivalent, relative to prednisolone in the presence or in the absence of an inert solvent in the presence of an organic tertiary base such as pyridine or triethylamine in an amount of about 1.0 equivalent relative to said acid halide to an amount sufficient as the solvent at about 0° C. to room temperature. As the inert solvent, there can be used, for example, hydrocarbons such as toluene, benzene and hexane; halogenated hydrocarbons such as carbon tetrachloride, chloroform, dichloromethane, dichloroethane and trichloroethylene; ethers such as diethyl ether, t-butyl methyl ether, diisopropyl ether, tetrahydrofuran and dimethoxyethane; ketones such as acetone and ethyl methylketone; aprotic polar solvents such as dimethylsulfoxide and dimethylformamide.

Reaction Example b

Reaction of prednisolone with a mixed acid anhydride of 2E,6E-farnesylic acid

Prednisolone 21-(2E,6E-farnesylate) can be produced by reacting prednisolone with a mixed acid anhydride of 2E 6E-farnesylic acid with pivalic acid, p-toluenesulfonic acid or the like in an amount of about 0.5 to 10 equivalent, preferably 0.9 to 2.0 equivalent, relative to prednisolone in the presence or absence of the same solvent as an inert solvent usable in Reaction Example a, preferably in the presence of an acid such as sulfuric acid or p-toluenesulfonic acid or a tertiary amine such as pyridine or triethylamine in a catalytic amount to an amount sufficient as the solvent at about 0° C. to room temperature.

Reaction Example C

Reaction of prednisolone with 2E,6E-farnesylic acid

Prednisolone 21-(2E,6E-farnesylate) can be obtained by reacting prednisolone with 2E,6E-farnesylic acid in an inert solvent such as benzene, toluene and xylene in the presence of a condensing agent such as dicyclohexylcarbodiimide or 2-chloro-1-methylpyridinium iodide and triethylamine at about 0° C. to under heating, or under conditions for azeotropic dehydration.

Reaction Example d

Reaction of prednisolone with a lower alkyl ester of 2E,6E-farnesylic acid

Prednisolone 21-(2E,6E-farnesylate) can be obtained by reacting prednisolone with a lower alkyl ester of 2E,6E-farnesylic acid in the presence of an esterexchange catalyst such as p-toluenesulfonic acid dr titanium metal compound such as tetramethyl titanate in an inert solvent such as toluene or xylene under heating while the resultant alcohol of lower boiling point is being removed from the reaction system.

Reaction Example e

Reaction of a halide, an alkanesulfonate or an arenesulfonate of prednisolone with an alkali metal salt, silver salt or a salt of an organic tertiary or quaternary base of 2E,6E-farnesylic acid Prednisolone 21-(2E,6E-farnesylate) can be obtained by reacting a halide, an alkanesulfonate or an arenesulfonate of prednisolone with an alkali metal salt, silver salt or a salt of an organic tertiary or quaternary base of 2E,6E-farnesylic acid in a solvent such as dimethylformamide, benzene, acetone or the like at about 0° C. to under heating.

As mentioned above, from the viewpoint of selectivity to and yield of prednisolone 21-(2E,6E-farnesylate) as the product, it is preferred that the reaction of prednisolone with 2E,6E-farnesylic acid is conducted in the presence of (disubstitued amino)pyridines and a condensing agent. The production method of prednisolone 21-(2E,6E-farnesylate) by this reaction will be described in detail hereunder.

As the (disubstituted amino)pyridines to be used in accordance with the present invention, adequates are the compounds of the general formula:

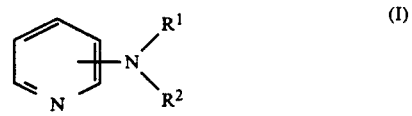

(wherein $R^1$ and $R^2$ designate independently an alkyl group or combinedly an alkylene group which may be substituted). As the alkyl group represented by $R^1$ and $R^2$ in the general formula (I), preferred are lower alkyl groups such as methyl, ethyl, propyl, isopropyl, butyl, isobutyl and sec-butyl. As the alkylene group represented by combined $R^1$ and $R^2$, there can be mentioned, for example, tetramethylene, pentamethylene and 3-methylpentamethylene. As the substituted alkylene group, there can be mentioned, for example, oxaalkylene such as 3-oxapentamethylene; and bis(disubstituted amino)methylene such as bis(dimethylamino)methylene and bis(diethylamino)-methylene. As the compound represented by the general formula (I), there are mentioned 4-(disubstituted amino)pyridines such as 4-(dimethylamino)pyridine, 4-(diethylamino)pyridine, 4-(N-ethyl-N-methylamino)pyridine, 4-(diisopropylamino)-pyridine, 4-(dibutylamino)pyridine, 4-(1-pyrrolidinyl)-pyridine, 4-piperidinopyridine, 4-(4-methyl-1-piperidinyl)pyridine, 4-(1-morpholino)pyridine and 1,1,3,3-tetramethyl-4-(4-pyridyl)-guanidine; and 2-(disubstituted amino)pyridines such as 2-(dimethylamino)pyridine and 2-piperidinopyridine.

In the reaction according to the present invention, as the condensing agent, there can be used such organic dehydration condensing agents as those usually used in ester-formation reactions between carboxylic acids and alcohols and coupling reaction such as peptide derivative-formation reaction between two species of peptide derivatives, two species of amino acid derivatives, or a peptide derivative and an amino acid derivative, which are exemplified by N,N'-disubstituted carbodiimides such as N,N'-dicyclohexylcarbodiimide, 1-ethyl-3-(3-dimethylaminopropyl)carbodiimide, N-cyclohexyl-N'-(2-morpholinoethyl)carbodiimide, N-cyclohexyl-N'-(4-dimethylaminocyclohexyl)carbodiimide, N,N'-diisopropylcarbodiimide and N-phenyl-N'-ethylcarbodiimide; 1-alkoxycarbonyl-2-alkoxy-1,2-dihydroquinolines such as 1-ethoxycarbonyl-2-ethoxy-1,2dihydroquinoline, quinoline, 1-isobutoxycarbonyl-2-ethoxy-1,2-dihydroquinoline and the like.

In the reaction of the present invention, 2E,6E-farnesylic acid is usually used in an amount ranging from about 0.1 to 10 mol, preferably from about 1 to 3 mol, relative to 1 mol of prednisolone. (Disubstituted amino)pyridines are usually used in an amount within the range of about 0.001 to 0.5 mol, preferably about 0.01 to 0.1 mol, relative to 1 mol of prednisolone. The amount of the condensing agent to be used is usually in the range from about 0.1 to 10 mol, preferably about 0.5 to 2 mol, relative to 1 mol of 2E,6E-farnesylic acid.

The above reaction is generally conducted in an organic solvent. As the organic solvent, there can be used ketones such as acetone and methyl ethyl ketone; esters such as ethyl acetate and methyl acetate; ethers such as diethyl ether, tetrahydrofuran, dioxane and dimethoxyethane; halogenated hydrocarbons such as dichloromethane, chloroform, carbontetrachloride, dichloroethane; hydrocarbons such as benzene, toluene and hexane; nitriles such as acetonitrile; amines such as pyridine and triethylamine singly or in a mixture of two or more species. Particularly, it is desirable to use ketones, esters, ethers, halogenated hydrocarbons and the like singly or in an admixture of two or more species since the selectivity to prednisolone 21-(2E,6E-farnesylate) and yield of the reaction in these solvents are high. The organic solvent may be usually used in an amount within the range from 0.1 to 1000 ml relative to 1 g of prednisolone. In case where the organic solvent is used in an amount within the range from about 1 to 100 ml relative to 1 g of prednisolone, the reaction procedure is convenient and the yield of prednisolone 21-(2E,6E-farnesylate) is high. The reaction can be usually conducted at a temperature within the range from about −70° C. to about 100° C., preferably within the range from about −20° C. to about 60° C. Particularly preferably, the reaction is conducted at a temperature within the range from about −10° C. to about 30° C., from the viewpoint of the height of the yield of prednisolone 21-(2E,6E-farnesylate) and the convenience of the reaction procedure. Though the reaction time varies depending upon the conditions such as reaction temperature, it usually ranges from about 1 to 200 hours.

Although in carrying out the reaction, there is no limitation to the order of mixing prednisolone, 2E,6E-farnesylic acid, (disubstituted amino)pyridines, the condensating agent and the organic solvent which is used, if necessary, in case where N,N'-disubstituted carbodiimides and the like as the condensing agent are used, it is preferable that the reaction is conducted while the condensing agent or the solution thereof in the organic solvent is slowly added to a mixture of prednisolone, 2E,6E-farnesylic acid, (disubstituted amino)pyridines and the organic solvent which is used if necessary under stirring, and that after the addition of the condensing agent or the solution thereof, the reaction is continued as necessary since the selectivity to prednisolone 21-(2E,6E-farnesylate) sometimes becomes high. Prednisolone 21-(2E,6E-farnesylate) can also be produced by reacting the mixture of 2E,6E-farnesylic acid and a condensing agent and mixing the resulting product with a (disubstituted amino)pyridine and prednisolone.

The resulting product obtained by the reaction of 2E,6E-farnesylic acid and a condensing agent is considered to be an acid anhydride derived from 2E,6E-farnesylic acid such as a symmetrical anhydride of 2E,6E-farnesylic acid, namely (E,E)-3,7,11-trimethyl-2,6,10-dodecatrienoic anhydride (hereinafter referred to as 2E,6E-farnesylic anhydride) or a mixed anhydride of 2E,6E-farnesylic acid and a condensing agent. The procedure of making to react 2E,6E-farnesylic acid and a condensing agent and subsequently to react the resulting product and prednisolone in the presence of a (disubstituted amino)pyridine will be hereinbelow explained in detail.

In the reaction of a condensing agent and 2E,6E-farnesylic acid, the amount of the condensing agent to be used is not always definite and varies depending on the kind of the condensing agent. Where such condensing agent as, for example, N,N'-disubstituted carbodiimides, which yields 2E,6E-farnesylic anhydride as a reaction product is used, it is preferably in the range of about 0.1 to 2.0 mol, more preferably, in the range of about 0.3 to 1.0 mol, based on 1 mol of 2E,6E-farnesylic acid. In further cases where a condensing agent considered to give, together with 2E,6E-farnesylic acid, a mixed acid anhydride as a reaction product, e.g., 1-alkoxycarbonyl-2-alkoxy-1,2-dihydroquinolines is used, the amount of it is preferred to be in the range of about 0.2 to 3.0 mol, more preferably in the range of about 0.5 to 1.5 mol against 1 mol of 2E,6E-farnesylic acid.

This reaction is usually carried out in an organic solvent such as ketones, esters, ethers, halogenated hydrocarbons, hydrocarbons, etc., whose amount to be used is ususally in the range of about 0.1 to 1000 ml, preferably in the range of about 0.5 to 100 ml against 1 g of 2E,6E-farnesylic acid. The reaction temperature is usually in the range of about −70° C. to 100° C., preferably in the range of about −20° C. to 60° C., more preferably in the range of about −10° C. to 30° C. The reaction time varies depending on the reaction conditions, but is usually in the range of about 1 to 30 hours.

In case where a condensing agent yielding 2E,6E-farnesylic anhydride as a reaction product is used, it is preferred that the condensing agent or a solution thereof in an organic solvent is added slowly while stirring to a mixture of 2E,6E-farnesylic acid and an organic solvent to cause reaction, and after the addition operation, the reaction is further continued, if necessary. This can advantageously enhance the selectivity rate to 2E,6E-farnesylic anhydride. Otherwise, in order to heighten the selectivity to 2E,6E-farnesylic anhydride and its yield, the reaction may be carried out in an organic solvent such as hydrocarbons, ethers, ketones, esters, etc. to which a salt of a tertiary amine and a strong acid, e.g., 4-(dimethylamino)pyridine hydrochloride is added in an amount of about 0.01 to 0.1 mol against 1 mol of 2E,6E-farnesylic acid.

The reaction mixture containing the reaction product obtained by the reaction of 2E,6E-farnesylic acid and a condensing agent in this manner can be used for the subsequent reaction with prednisolone as it is or after the organic solvent has been distilled off. Alternatively, the reaction product separated from the reaction mixture by subjecting to separation operation, e.g., column chromatography may be used for the reaction with prednisolone.

2E,6E-Farnesylic anhydride is relatively stable and can be relatively readily isolated from the reaction mixture, whereas the mixed anhydride of 2E,6E-farnesylic acid and a condensing agent is susceptible to decomposition during separation operation. Accordingly, where such a condensing agent that is considered to yield such mixed anhydride as a reaction product is used, the reaction mixture is preferably provided as such for the reaction with prednisolone.

Where 2E,6E-farnesylic acid and a condensing agent were made to react in the presence of a salt of a tertiary amine and a strong acid, it is preferred to remove the salt, for example, by liquid-liquid partition method, from the viewpoint of the selectivity to prednisolone 21-(2E,6E-farnesylate), so as not to contaminate the subsequent reaction sysytem in which prednisolone is used.

In the reaction between the foregoing reaction product of 2E,6E-farnesylic acid and a condensing agent and prednisolone in the presence of (disubstituted amino)-pyridine, the amount of prednisolone is usually in the range of about 0.05 to 2.0 mol, preferably in the range of about 0.2 to 1.1 mol against 1 mol of 2E,6E-farnesylic acid initially used or 1 mol of 2E,6E-farnesylic anhydride separated.

The amount of (disubstituted amino)pyridine to be used is usually in the rang of about 0.001 to 0.5 mol, preferably in the range of about 0.01 to 0.1 mol against 1 mol of prednisolone as stated previously. This reaction is carried out usually in the presence of an organic solvent such as ketones, esters, ethers, halogenated hydrocarbons, nitriles, amines, etc., whose amount to be used is usually about 0.1 to 1000 ml, preferably about 1 to 100 ml against 1 g of prednisolone. The reaction temperature is usually in the range of about $-50°$ C., to $100°$ C., preferably about $0°$ C. to $50°$ C. The reaction time varies depending on the reaction conditions, but is usually in the range of about 5 to 200 hours.

The separation and purification of prednisolone 21-(2E,6E-farnesylate) obtained by the above-mentioned estersynthesis reactions can be conducted by the conventional method. For example, water is added to the reaction mixture, followed by extraction with ethyl acetate or the like. After the extract is washed with water and dried, the solvent is distilled off. The residue is subjected to separation, for example, by column chromatography to give prednisolone 21-(2E,6E-farnesylate). In case where thus-obtained prednisolone 21-(2E,6E-farnesylate) is contaminated with geometrical isomers of prednisolone 21-(2E,6E-farnesylate) which are formed in the ester-synthesis reaction, prednisolone 21-(2E,6E-farnesylate) can be purified by, for example, washing with diethyl esther or recrystallizing from a solvent such as a mixed solvent of ethyl acetate and hexane or diethyl ether.

When the 2E,6E-farnesylic acid or its reactive derivative to be used for producing prednisolone 21-(2E,6E-farnesylate), are those free of its geometrical isomers as impurities and of high purity, prednisolone 21-(2E,6E-farnesylate) is sometimes produced in high yield on the basis of prednisolone. However, as 2E,6E-farnesylic acid or its reactive derivative, a mixture of 2E,6E-farnesylic acid or its reactive derivative with geometrical isomers thereof can be used.

2E,6E-Farnesylic acid which is used as the starting compound in the reaction in accordance with the present invention can be easily obtained by the oxidizing (E,E)-3,7,11-trimethyl-2,6,10-dodecatrienal with chlorous acid in accordance with the method described in the gazette of Japanese Patent Application Laid-open (Kokai) No. 142137/1987.

Next, shown are the test and the results for antiinflammatory activities of prednisolone 21-(2E,6E-farnesylate) of the compound of the present invention and prednisolone, 11$\beta$,17$\alpha$,21-trihydroxy-1,4-pregnadiene-3,20-dione 21-[(Z,Z)-3,7.11-trimethyl-2,6,10-dodecatrienoate][hereinafter referred to as prednisolone 21-(2Z,6Z-farnesylate)] or 11$\beta$,17$\alpha$,21-trihydroxy-1,4-pregnadiene-3,20-dione 21-[(Z,E)-3,7,11-trimethyl-2,6,10-dodecatrienoate [hereinafter referred to as prednisolone 21-(2Z,6E-farnesylate)] which was used as a compound for comparison.

TEST EXAMPLE 1

Cotton pellet granuloma test

A cotton pellet was impregnated with the ethanol solution of a compound to be tested, dried and sterilized in autoclave. In one group of 10 Wistar male rats (weight 142–164 g), each rat was incised a little along the back median line under etherization and 30 ± 1 mg of each one of the above-mentioned cotton pellet was inserted under the skin of both sides of shoulder. At the 7th day after the insertion of the cotton pellet, the rat was killed, the granuloma and thymus were removed, and their weights were measured. Concerning the granuloma, it was weighed after drying, and the value had after subtracting the weight of the cotton pellet from the weight weighed was considered to be the weight of granuloma (two of left and right). As a control, the similar test was performed with a cotton pellet impregnated with ethanol without the compound to be tested, dried and sterilized in autoclave. Table 1 shows the results of these tests.

TABLE 1

| Test compound | Application amount (μg/pellet) | Body weight increase (g) | Granuloma weight (mg) mean ± S.D. | Granuloma growth inhibition rate (%) | Thymus weight (mg) mean ± S.D. | Thymus weight (mg/100 g weight) mean ± S.D. |
| --- | --- | --- | --- | --- | --- | --- |
| Control | — | 35.9 ± 3.48 | 101.7 ± 9.82 | — | 451.2 ± 50.61 | 239.1 ± 24.42 |
| Compound of | 1 | 38.1 ± 3.51 | 94.2 ± 14.45 | 7.4 | 435.8 ± 46.45 | 228.5 ± 23.78 |
| Invention [prednisolone 21-(2E,6E-farnesylate)] | 100 | 39.1 ± 3.87 | 28.3 ± 5.01* | 72.2# | 428.6 ± 44.57 | 225.7 ± 22.08 |
| Compound for comparison (prednisolone) | 100 | 35.5 ± 4.86 | 55.4 ± 13.94* | 45.5 | 408.4 ± 52.97 | 217.5 ± 25.84 |

*Significant difference between Control, $p < 0.001$
Significant difference between Compound for comparison, $p < 0.001$ As shown in Table 1, the prednisolone 21-(2E,6E-farnesylate) of the present invention was remarkably high in antiinflammation activity compared to the prednisolone for comparison, while the involution action to the thymus was reduced.

TEST EXAMPLE 2

Adjuvant arthritis test

In 30 Lewis male rats (weight 195-245 g), the inoculation of 0.1 ml of adjuvant prepared by suspending $R_{35}H_5$ dead tubercule bacilli at the concentration of 5 mg/ml in liquid paraffin in the tail base skin of each rat caused arthritis. At the 15th day after the inoculation, the limb volume was measured, and rats of the similar volume in the right hindlimb were divided into three groups (10 rats per group). Each 100 mg of gel ointment containing a compound to be tested, which ointment was prepared according to the method in Example 34 described later, was applied to the right hindlimb of rats at one time a day from the 15th to 22nd day after the inoculation. The volume of the right hindlimb of rats was measured at 18th, 20th, 22nd, 25th, 27th and 29th day after the inoculation. As a control, the same test was performed except no application of the gel ointment. FIG. 1 shows the results of these tests. In FIG. 1, the longitudinal axis indicates the average right hindlimb volume of the rats in each of the groups.

As shown in FIG. 1, prednisolone 21-(2E,6E-farnesylate) of the invention is more remarkably excellent in the activity and continuation of anti-inflammatory action compared with the prednisolone 21-(2Z,6Z-farnesylate) for comparison.

TEST EXAMPLE 3

Test for the inhibition of thymidine incorporation into human lymphocyte subjected to blast transformation.

The intensity of steroid in the inhibiting action against thymidine incorporation into human lymphocyte subjected to blast transformation was expected as an index of the antiinflammation activity of the said steroid. [Medicina, vol. 22, No. 7 (1985)pp. 1174–1175 and Medio, vol. 4, No. 8 (1987) pp. 78–92]

According to the method described in Clinical and Experimental Immunology, vol. 15 (1973) pp. 203–212, prednisolone 21-(2E,6E-farnesylate) of the invention, prednisolone 21-(2Z,6Z-farnesylate) for comparison, and predinisolone 21-(2Z,6E-farnesylate) for comparison were evaluated for the inhibiting action against thymidine incorporation into human lymphocyte subjected to blast transformation by phytohemagglutinin. Lymphocyte isolated from human peripheral blood was floated at the concentration of $3.3 \times 10^5$ lymphocyte/ml in RPMI-1640 culture solution containing fetal bovine serum of the concentration of 20 vol.%. To 2 ml of the mixture thus obtained, 20 μl of the ethanol solution of a compound to be tested was added, and the mixture was cultured for 30 minutes at 37° C. in the atmosphere containing carbon dioxide of the concentration of 5 vol.%. To the mixture thus obtained, 20 μl of RPMI-1640 culture solution containing phytohemagglutinin of the concentration of 1 mg/ml was added, and the mixture was cultured for 3 days at 37° C. in the atmosphere containing carbon dioxide of the concentration of 5 vol.%. To the mixture thus obtained, 200 μl of thymidine labelled with $^3H$ (radioactivity; 10 microcurie/ml) was added, and the mixture was further cultured for 4 hours. The lymphocyte in the mixture thus obtained was obtained as precipitate by washing three times with physiological saline. To the precipitate thus obtained, 0.25 ml of the 0.5 normal toluene solution of quaternary ammonium hydroxide (Soluene-350 made in Packard Co., U.S.A.) and 5 ml of the cocktail agent containing pseudocumene (Hionic-Flour made in Packard Co., U.S.A.) were added, then the amount of thymidine labelled with $^3H$ incorporated into the lymphocyte was measured by a scintillation counter. Based on the amount of thymidine incorporated into the lymphocyte, the inhibition rate against thymidine incorporation was calculated on the basis of the amount of thymidine measured in the same test except no addition of the compound to be tested. FIG. 2 shows these results. The horizontal axis indicates the concentration of the test compounds in the mixture which was obtained by adding thymidine labelled with $^3H$.

As shown in FIG. 2, prednisoone 21-(2E,6E-farnesylate) of the invention as stronger in the inhibiting action against thymidine incorporation into human lymphocyte subjected to blast transformation by phytohemagglutinin compared to prednisolone 21-(2Z,6Z-farnesylate) and prednisolone 21-(2Z,6E-farnesylate) for comparison.

Prednisolone 21-(2E,6E-farnesylate) has been confirmed to have excellent characteristics as an antiinflammation agent and a low toxicity in a toxicity test. The acute toxicity of prednisolone 21-(2E,6E-farnesylate) [$LD_{50}$(ddy male mice, weight 23.6–26.2 g, 5 mice per group, subcutaneous injection)] was not less than 2,000 mg/kg.

From the results of the foregoing pharmacological test, prednisolone 21-(2E,6E-farnesylate) is found to be useful as a medicine for treating inflammations caused by various factors.

According to this invention, medicinal compositions containing prednisolone 21-(2E,6E-farnesylate) can be provided. The medicinal compositions may be administered orally or parenterally. The compositions for oral administration may be in the form of powders, tablets, emulsions, capsules, granules, liquids (including tinctures, fluid-extracts, medicated spirits, suspensions, limonades, syrups and the like) and so on. The parenteral compositions may be in the forms such as injectable preparations, preparations for instillation, ointments, plasters, liquids (including medicated spirits, tinctures, lotions and the like), cataplasms, appliable preparations, sprays, dusting powders, liniments, creams, emulsions, solutions and so on.

Though the dosage varies depending upon the sympton, in the case of oral compositions, injectable preparations and preparations for instillation, the daily dosage can be in the range from 1 to 500 mg, preferably 5 to 100 mg per human adult as prednisolone 21-(2E,6E-farnesylate). The composition can be administered at this dosage, in single dose or in divided dose several times a day. In the case of parenterally external application, the composition may be used at a concentration of 0.01 to 10%, preferably 0.1 to 3%, on the basis of prednisolone 21-(2E,6E-farnesylate).

Prednisolone 21-(2E,6E-farnesylate) of the present invention can be used alone or as the pharmaceutical preparations which contain one or more species of appropriate bases such as carriers and excipients. Such pharmaceutical preparations include oral medicines, injectable preparations and externally applicable preparations and the like. These pharmaceutical preparations can be prepared in the conventional manner using conventional bases.

As the form for oral medicines, there may be mentioned tablets, capsules, powders, granules, liquids and the like. The excipients to be used for the production of these forms of pharmaceutical preparations include, for example, lactose, sucrose, starch, crystalline cellulose, white sugar, sodium chloride, glucose solution, calcium carbonate, kaolin and the like. As the binders to be used, there may be mentioned, for example, polyvinyl alcohol, methylcellulose, ethylcellulose, carboxymethyl cellulose, polyvinyl pyrrolidione, gum arabic, shellac, white sugar and the like. As the lubricants to be used, there may be mentioned, for example, forix acid powder, solid polyethylene glycol, magnesium stearate, talc and the like. Furthermore, these pharmaceutical preparations may comprise coloring agents, disintegrators, corrigents and the like which are conventionally used. The tablets may be coated in the conventional manner.

In producing injectable preparations, as the solvent, there may be used, for example, water, ethyl alcohol, polyethylene glycol, propylene glycol, polyoxyethylene sorbitan fatty acid esters and the like. In this case, sodium chloride, glucose, glycerol and the like may be contained in an amount sufficient enough to prepare an isotonicized solution. Also, pH-adjusting agents, buffers, stabilizers and the like which are conventionally used may be added. The above injectable preparations can be topically, for example, as intra-articular injections, used in the form of injectable suspension.

As the forms of externally applicable preparations, there may be ointments (greasy ointment, emulsified ointment, water-soluble ointment and the like), liquid liniments, lotions, powders, adhesives, sprays, inhalants, suppositories and the like. As for the ointments, it is possible to obtain those in suitable form by using one or more species of grease, greasy oil, vaseline, paraffin, wax, lanolin, alcohols, clay-minerals, surfactants, water and the like as the base. The pH value of the ointments is preferably in the range of 6 to 7.5 from the viewpoint of restriction on coloring, and more preferaly in the range of 6.5 to 7. It is desirable that the ointments comprise in order to enhance penetration of prednisolone 21-(2E,6E-farnesylate) into the diseased portion, penetration-enhancing agents such as a dicarboxylic acid diester (e.g., diethyl sebacate, diisopropyl sebacate, diisopropyl adipate, diethyl adipate); a monocarboxylic acid ester (e.g., isopropyl myristate, isopropyl palmitate); N-ethyl-N-(2-methylphenyl)-2-butenamide, 1-dodecylazacycloheptan-2-one, squalane, urea, lecithin and so on. It is also preferable that the ointments being in gel form in view of the excellent absorption of prednisolone 21-(2E,6E-farnesylate) into the diseased portion. Said gel ointments comprise, for example, prednisolone 21-(2E,6E-farnesylate); a glycol such as propylene glycol, butylene glycol, a polyethylene glycol having a molecular weight of below 1000 (e.g., macrogol 400, etc.); a thickener such as a carboxyvinyl polymer, a cellulose polymer (e.g., a hydroxypropylmethylcellulose, a hydroxypropylcellulose, etc.), a polyethylene glycol having a molecular weight of not less than 1000 (e.g., macrogol 1500, macrogol 4000, macrogol 6000, etc.); an alcohol such as a lower alcohol (e.g., isopropyl alcohol, ethanol, etc.); afore-mentioned penetration-enhancing agent; and purified water. The amount of prednisolone 21-(2E,6E-farnesylate) in said gel ointments is preferably 0.01 to 10 weight % and more preferably, 0.1 to 3 weight %. The amount of a glycol in said gel ointments is preferably 5 to 30 weight % and more preferably, 10 to 20 weight %. It is also preferable that a thickener is incorporated in said gel ointments at an amount of 0.1 to 5 weight %. As a thickener, a carboxyvinyl polymer is used alone or a carboxyvinyl polymer, a cellulose polymer and a polyethylene glycol having a molecular weight of not less than 1000 are used combinedly in an amount of 0.1 to 4 weight %, 0.1 to 4 weight % and 0.1 to 3 weight % respectively and more preferably, at an amount of 0.5 to 2 weight %, 0.5 to 2 weight % and 0.5 to 1.5 weight %. An alcohol is preferably used in an amount of 10 to 70 weight % of said gel ointments and more preferably, at an amount of 30 to 60 weight %. A penetration-enhancing agent is preferably used in an amount of 1 to 10 weight % of said gel ointments and more preferably used in an amount of 3 to 7 weight %. The amount of purified water is preferred to be 10 to 50 weight % of the gel ointments and more preferably, 20 to 40 weight %. The pH-adjusting agents such as an amine (e.g., triisopropanolamine, diisopropanolamine, etc.), ammonia, sodium hydroxide and so on; and UV absorbents such as 2-hydroxy-4-methoxybenzophenone, ethyl p-aminobenzoate and so on may be used as necessary in the gel ointments. As the liquid liniments, there may be mentioned aqueous liquids as prepared by using, for example, water and water-miscible solvent as the base and, if necessary, further by using an appropriate auxiliary solubilizer, liquids as prepared by using glycerol or propyleneglycol as the base, tinctures as prepared by using an alcohol as the base and the like. As the lotions, there may be mentioned suspension-type lotions, emulsion-type lotions and the like, which can be prepared by using one or more species of emulsifying agents, suspending agents (e.g. dispersant, thickening agent, humidifying agent), protecting agents together with water. The powders can be prepared by using appropriate powdery bases such as talc, kaolin, starch and zinc oxide. As the adhesives, there may be mentioned, for example, cataplasms or adhesive tapes in which prednisolone 21-(2E,6E-farnesylate) of the present invention is incorporated. As the sprays and inhalants, there may be mentioned aerosols as produced by dissolving or suspending prednisolone 21-(2E,6E-farnesylate) of the present invention in a suitable solvent and adding an appropriate propellant such as fluorocarbon, carbon dioxide gas, or liquefied petroleum gas, sprays which can be sprayed with the use of an appropriate spraying bomb and the like. The suppositories can be prepared by using grease such as cacao butter, lanolin and fatty acid triglyceride; polyethylene glycol; gelatin and the like as the base.

As evident from the above-mentioned results of the pharmacological tests, prednisolone 21-(2E,6E-farnesylate) which can be provided in accordance with the present invention exhibits remarkably excellent antiinflammatory action as compared with prednisolone and the geometrical isomers of prednisolone 21-farnesylate other than prednisolone 21-(2E,6E-farnesylate) as control compounds, and besides, displays reduced side effects which are found with prednisolone. The antiinflammatory compositions containing prednisolone 21-(2E,6E-farnesylate) of the present invention premits the excellent antiinflammatory action possessed by said prednisolone 21-(2E,6E-farnesylate) to exhibit effectively.

Also, according to the production method of the present invention, prednisolone 21-(2E,6E-farnesylate) can be produced in high selectivity and good yield and conveniently, as is evident from the examples described later.

EXAMPLES

Hereafter the present invention is concretely described by illustrating examples, which are not to be construed as being limitative.

EXAMPLE 1

A solution consisting of 37.14 g (190 mmol) of N,N'-dicyclohexylcarbodiimide and 150 ml of tetrahydrofuran was added dropwise to a mixture of 36.05 g (100 mmol) of prednisolone, 44.91 g (190 mmol) of 2E,6E-farnesylic acid, 0.611 g (5.0 mmol) of 4-(dimethylamino)pyridine and 150 ml of dichloromethane while stirring under ice-cooling over the period of 9 hours. After the completion of dropwise addition, the reaction mixture was stirred for further 3 days at room temperature. A portion of the thus-obtained reaction mixture was subjected to analysis by high performance liquid chromatography, and it was found that the residual amount of prednisolone in the reaction mixture was 0.03 g (0.07 mmol) and the yield of prednisolone 21-farnesylate was 57.5 g (100 mmol). As the result of the analysis with high performance liquid chromatography of a portion of the obtained prednisolone 21-farnesylate, it was found that said prednisolone 21-farnesylate was a mixture of prednisolone 21-(2E,6E-farnesylate) and prednisolone 21(2Z,6E-farnesylate) (molar ratio: 89 to 11). The obtained dicyclohexylurea was removed by filtration of the reaction mixture. The filtrate was concentrated under reduced pressure and 250 ml of ethyl acetate was added to the obtained concentrate to dissolve it under heating. The solution was filtered while it remained heated. At a temperature from about 60° C. to 70° C., 500 ml of hexane was added dropwise to the obtained filtrate. After the completion of dropwise addition, the mixture was gradually cooled to room temperature. The precipitated crystals were collected by filtration, and recrystallized from 160 ml of methanol to give 30.76 g (53.2 mmol) of prednisolone 21-(2E,6E-farnesylate) as white crystals. Further, the whole mother liquid was recovered and subjected to recrystallization from ethyl acetate-hexane and methanol to afford 13.87 g (24.0 mmol) of prednisolon 21-(2E,6E-farnesylate) as white crystals. The thus-obtained prednisolon 21-(2E,6E-farnesylate) has the following properties and the yield thereof was 77% on the basis of the consumed prednisolone.

m.p.: 152–154° C.

FD-Mass spectrum: 578(M+)

$^1$H-NMR spectrum (500 MHz) $\delta_{TMS}^{CDCl_3}$: 7.29 (d, J=10Hz, 1H); 6.28 (d, J=10Hz, 1H); 6.02 (s, 1H); 5.81 (s, 1H); 5.10 (m, 2H); 5.05 (d, J=18Hz, 1H); 4.89 (d, J=18Hz, 1H); 4.49 (m, 1H); 2.17 (s, 3H); 1.70 (s, 3H); 1.63 (s, 6H); 1.47 (s, 3H); 1.00 (s, 3H)

$^{13}$C-NMR spectrum (125MHz) $\delta^{CD_3OD}$: 206.4, 187.9, 173.6, 166.5, 161.4, 159.0, 136.3, 131.2, 126.8, 124.4, 123.2, 121.5, 115.1, 89.7, 69.9, 67.5, 56.4, 51.9, 45.1, 40.9, 39.8, 39.3, 34.6, 33.7, 32.2, 31.7, 26.8, 26.0, 24.9, 23.9, 20.63, 20.57, 18.1, 16.8, 16.3, 15.2

EXAMPLE 2

Prednisolone [36.05 g (100 mmol)] and 44.91 g (190 mmol) of 2E,6E-farnesylic acid were reacted in the same manner as in Example 1. Dicyclohexylurea was removed by filtrating the obtained reaction mixture. The filtrate was concentrated under reduced pressure, and the obtained concentrate was subjected to silica gel column chromatography (developing solvent: a mixed solvent of ethyl acetate and hexane) to give 56.6 g (97.9 mmol) of prednisolone 21-farnesylate. Also, 0.05 g (1.4 mmol) of prednisolone was recovered. As the result of the analysis with high performance liquid chromatography of a portion of the obtained prednisolone 21-farnesylate, it was found that said prednisolone 21-farnesylate was a mixture of prednisolone 21-(2E,6E-farnesylate) and prednisolone 21-(2Z,6E-farnesylate) (molar ratio: 89 to 11). This prednisolone 21-farnesylate was washed with diethyl ether to afford 45.1 g (78.0 mmol) of prednisolone 21-(2E,6E-farnesylate) as a white solid. The yield of the isolated prednisolone 21-(2E,6E-farnesylate) was 79% on the basis of the consumed prednisolone.

EXAMPLE 3

To a mixture of 3.6 g (10 mmol) of prednisolone, 3.5 g (15 mmol) of 2E,6E-farnesylic acid, 0.085 g (0.70 mmol) of 4-(dimethylamino)pyridine and 15 ml of dichloromethane was added at once 3.1 g (15 mmol) of N,N'-dicyclohexylcarbodiimide, and the mixture was stirred at room temperature for 12 hours. As the result of analysis with high performance liquid chromatography of a portion of the obtained reaction mixture, it was found that the residual amount of prednisolone in the reaction mixture was 0.36 g (1.0 mmol) and the yield of prednisolone 21-farnesylate was 5.2 g (9.0 mmol). Dicyclohexylurea was removed by filtrating the reaction mixture. The filtrate was concentrated under reduced pressure, and the obtained concentrate was subjected to silica gel column chromatography (developing solvent: a mixed solvent of ethyl acetate and hexane) to give 5.1 g (8.8 mmol) of prednisolone 21-farnesylate. As the result of analysis with high performance liquid chromatography of a portion of prednisolone 21-farnesylate, it was found that said prednisolone 21-farnesylate was a mixture of prednisolone 21-(2E,6E-farnesylate) and prednisolone 21-(2Z,6E-farnesylate) (molar ratio: 89 to 11).

This prednisolone 21-farnesylate was washed with diethyl ether to give 3.6 g (6.2 mmol) of prednisolone 21-(2E,6E-farnesylate) as a white solid. The yield of the isolated prednisolone 21-(2E,6E-farnesylate) was 69% on the basis of the consumed prednisolone.

EXAMPLES 4 TO 11

By conducting the reaction and separation-purification procedure in the same manner as in Example 3 using (disubstituted amino)pyridines in the amount indicated in Table 2 respectively in place of 0.085 g (0.70 mmol) of 4-(dimethylamino)pyridine in Example 3, prednisolone 21-(2E,6E-farnesylate) was obtained. The results are shown in Table 2.

TABLE 2

| Example | Used (disubstituted amino)pyridine Species (Chemical structure) | Amount | Residual amount of prednisolone (g) (Note 1) | Yield of prednisolone 21-farnesylate (g) (Note 2) | Prednisolone 21-(2E,6E-farnesylate) Yield (g) (Note 3) | Prednisolone 21-(2E,6E-farnesylate) Yield (%) (Note 4) |
|---|---|---|---|---|---|---|
| 4 | 4-N(CH₃)₂-pyridine | 0.35 g (2.9 mmol) | 0.25 | 5.3 | 3.2 | 59 |
| 5 | 4-N(C₂H₅)₂-pyridine | 0.105 g (0.70 mmol) | 0.30 | 5.2 | 3.6 | 67 |
| 6 | 4-(piperidin-1-yl)pyridine | 0.113 g (0.70 mmol) | 0.36 | 5.1 | 3.5 | 68 |
| 7 | 4-(pyrrolidin-1-yl)pyridine | 0.104 g (0.70 mmol) | 0.33 | 5.2 | 3.5 | 67 |
| 8 | 4-(4-methylpiperidin-1-yl)pyridine | 0.123 g (0.70 mmol) | 0.34 | 5.2 | 3.5 | 67 |
| 9 | 4-(morpholin-4-yl)pyridine | 0.115 g (0.70 mmol) | 0.37 | 5.1 | 3.4 | 66 |
| 10 | 4-[N=C(N(CH₃)₂)₂]pyridine | 0.134 g (0.70 mmol) | 0.35 | 5.2 | 3.5 | 67 |
| 11 | 2-N(CH₃)₂-pyrimidine/pyridazine analogue | 0.012 g (0.10 mmol) | 1.80 | 2.7 | 1.8 | 62 |

(Note 1)
A quantitative analysis was conducted by subjecting a portion of the reaction mixture to high performance liquid chromatography.
(Note 2)
Shown is the yield of a mixture of prednisolone 21-(2E,6E-farnesylate) and prednisolone 21-(2Z,6E-farnesylate)(The molar ratio in every example was about 9 to 1.) as obtained by subjecting the concentrate of the filtrate of the reaction mixture to silica gel column chromatography.
(Note 3)
Shown is the yield of the isolated prednisolone 21-(2E,6E-farnesylate).
(Note 4)
Shown is the yield of the isolated prednisolone 21-(2E,6E-farnesylate) on the basis of the consumed prednisolone.

EXAMPLE 12

To a mixture of 3.6 g (10 mmol) of prednisolone, 3.5 g (15 mmol) of 2E,6E-farnesylic acid, 60 mg (0.5 mmol) of 4-(dimethylamino)pyridine and 20 ml of dichloromethane was added 2.3 g (15 mmol) of 1-ethyl-3-(3-dimethylaminopropyl)-carbodiimide, and the mixture was stirred at room temperature for 48 hours. The solvent was distilled off from the reaction mixture. The obtained residue was dissolved in ethyl acetate, washed with diluted hydrochloric acid, an aqueous solution of sodium bicarbonate and an aqueous solution of sodium chloride in this sequence and dried over anhydrous sodium sulfate. The solvent was distilled off to give the residue, which was subjected to silica gel column chromatography (developing solvent: a mixed solvent of ethyl acetate and hexane) to give 4.8 g (8.3 mmol) of prednisolone 21-farnesylate. Also, 0.18 g (0.5 mmol) of prednisolone was recovered. As the result of analysis with high performance liquid chromatography, it was found that the obtained prednisolone 21-farnesylate was a mixture of prednisolone 21-(2E,6E-farnesylate) and prednisolone 21-(2Z,6E-farnesylate) (molar ratio: 88 to 12). This prednisolone 21-farnesylate was recrystallized from a mixed solvent of ethyl acetate and hexane to give 3.6 g (6.2 mmol) of prednisolone 21-(2E,6E-farnesylate) as white crystals. The yield of the isolated prednisolone 21-(2E,6E-farnesylate) was 65% on the basis of the consumed prednisolone.

EXAMPLES 13 AND 14

By conducting the reaction procedure and separation-purification procedure in the same manner as in Example 12 using the condensing agents indicated in Table 3 respectively in place of 2.3 g (15 mmol) of 1-ethyl-3-(3-dimethylaminopropyl)-carbodiimide, prednisolone 21-(2E,6E-farnesylate) was obtained. The obtained results are shown in Table 3.

TABLE 3

| Example | Used condensing agent Species | Amount | Yield of prednisolone 21-farnesylate (g) (Note 1) | Amount of recovered prednisolone (g) (Note 2) | Prednisolone 21-(2E,6E-farnesylate) Yield (g) (Note 3) | Prednisolone 21-(2E,6E-farnesylate) Yield (%) (Note 4) |
|---|---|---|---|---|---|---|
| 13 | N-Cyclohexyl-N'-(2-morpholino-ethyl)carbodiimide | 3.6 g (15 mmol) | 5.0 | 0.35 | 3.5 | 68 |
| 14 | N-Cyclohexyl-N'-(4-dimethylamino-cyclohexyl)-carbodiimide | 3.7 g (15 mmol) | 5.1 | 0.30 | 3.7 | 70 |

(Note 1)
Shown is the yield of the mixture of prednisolone 21-(2E,6E-farnesylate) and prednisolone 21-(2Z,6E-farnesylate) (The molar ratio in every example was about 9 to 1) as obtained by subjecting the mixture obtained by the post-treatment of the reaction mixture to silica gel column chromatography.
(Note 2)
Shown is the amount of prednisolone recovered by subjecting the mixture obtained by post-treatment of the reaction mixture to silica gel column chromatography.
(Note 3)
Shown is the yield of the isolated prednisolone 21-(2E,6E-farnesylate).
(Note 4)
Shown is the yield of the isolated prednisolone 21-(2E,6E-farnesylate) on the basis of the consumed prednisolone.

EXAMPLES 15 TO 17

By conducting the reaction procedure and separation-purification procedure in the same manner as in Example 3 using 15 ml of the organic solvents as indicated in Table 4 respectively in place of 15 ml of dichloromethane as the reaction solvent in Example 3, prednisolone 21-(2E,6E-farnesylate) was obtained. The obtained results are shown in Table 4.

TABLE 4

| Example | Organic solvent | Residual amount of prednisolone (g) (Note 1) | Yield of prednisolone 21-farnesylate (g) (Note 2) | Prednisolone 21-(2E,6E-farnesylate) Yield (g) (Note 3) | Prednisolone 21-(2E,6E-farnesylate) Yield (%) (Note 4) |
|---|---|---|---|---|---|
| 15 | Mixed solvent of dichloromethane and tetrahydrofuran (volume ratio: 1 to 1) | 0.58 | 4.7 | 3.5 | 71 |
| 16 | Mixed solvent of dichloromethane and ethyl acetate (volume ratio: 1 to 1) | 1.15 | 3.8 | 2.9 | 75 |
| 17 | Acetone | 0.58 | 4.7 | 3.1 | 64 |

(Note 1)
The quantitative analysis was conducted by subjecting a portion of the reaction mixture to high performance liquid chromatography.
(Note 2)
Shown is the yield of a mixture of prednisolone 21-(2E,6E-farnesylate) and prednisolone 21-(2Z,6E-farnesylate)(The molar ratio in every example was about 9 to 1.) as obtained by subjecting the concentrate of the filtrate of the reaction mixture to silica gel column chromatography.
(Note 3)
Shown is the yield of the isolated prednisolone 21-(2E,6E-farnesylate).
(Note 4)
Shown is the yield of the isolated prednisolone 21-(2E,6E-farnesylate) on the basis of the consumed prednisolone.

EXAMPLE 18

To a mixture of 4.0 g (17 mmol) of 2E,6E-farnesylic acid, 3.6 g (10 mmol) of prednisolone, 85 mg (0.7 mmol) of 4-(dimethylamino)pyridine and 20 ml of anhydrous tetrahydrofuran was added 4.2 g (17 mmol) of 1-ethoxycarbonyl-2-ethoxy-1,2-dihydroquinoline under ice-cooling, and the mixture was stirred under ice-cooling for an hour and further stirred at room temperature for 72 hours. The solvent was distilled off from the reaction mixture to give the residue, which was dissolved in ethyl acetate and washed with diluted hydrochloric acid, an aqueous solution of sodium bicarbonate and an aqueous solution of sodium chloride in this sequence and dried over anhydrous sodium sulfate. The solvent was distilled off. The obtained residue was subjected to silica gel column chromatography (developing solvent: a mixed solvent of ethyl acetate and hexane) to give 2.73 g (4.7 mmol) of prednisolone 21-farnesylate. Also, 1.55 g (4.3 mmol) of prednisolone was recovered. As the result of analysis with high performance liquid chromatography, it was found that the obtained prednisolone 21-farnesylate was a mixture of prednisolone 21-(2E,6E-farnesylate) and prednisolone 21-(2Z,6E-farnesylate) (molar ratio: 90 to 10). This prednisolone 21-farnesylate was washed with ether to give 2.26 g (3.9 mmol) of prednisolone 21-(2E,6E-farnesylate) as a white solid. The yield of the isolated prednisolone 21-(2E,6E-farnesylate) was 68% on the basis of the consumed prednisolone.

EXAMPLES 19 AND 20

By conducting the reaction procedure and separation-purification procedure in the same manner as in Example 18 using the condensing agents indicated in Table 5 respectively in place of 4.2 g (17 mmol) of 1-ethoxycarbonyl-2-ethoxy-1,2-dihydroquinoline, prednisolone 21-(2E,6E-farnesylate) was obtained. The obtained results are shown in Table 5.

resulting mixture was stirred at room temperature for further 3 days. A portion of the reaction mixture solution thus obtained was analyzed by high performance liquid chromatography and as a result, it was found that the residual amount of prednisolone in the mixture was 0.11 g (0.3 mmol); and the yield of prednisolone 21-farnesylate was 57.2 g (99.0 mmol). The prednisolone 21-farnesylate was proved to be a mixture of prednisolone 21-(2E,6E-farnesylate) and prednisolone 21-(2Z,6E-farnesylate)(molar ratio: 93 to 7). To the residue obtained by distilling off the solvent from the reaction mixture was added 250 ml of ethyl acetate, and the residue was dissolved under heating and filtered while it remained heated. To the obtained filtrate, 500 ml of hexane was added dropwise at about 60° C. to 70° C. and then, gradually cooled to room temperature. The precipitated crystals were separated by filtration and subjected to recrystallization from 160 ml of methanol. Prednisolone 21-(2E,6E-farnesylate), 29.94 g (51.8 mmol), was obtained as white crystals. The yield of the isolated prednisolone 21-(2E,6E-farnesylate) was 52% on the basis of the consumed prednisolone.

TABLE 5

| Example | Condensing Agents Species (Structural formula) | Amount | Residual amount of prednisolone (g) (Note 1) | Yield of prednisolone 21-farnesylate (g) (Note 2) | Prednisolone 21-(2E,6E-farnesylate) Yield (g) (Note 3) | Prednisolone 21-(2E,6E-farnesylate) Yield (%) (Note 4) |
|---|---|---|---|---|---|---|
| 19 | (quinoline derivative with N—OCH₃, N-COOCH₂CH(CH₃)₂) | 4.4 g (17 mmol) | 1.6 | 2.7 | 2.2 | 69 |
| 20 | (quinoline derivative with N—OC₂H₅, N-COOCH₂CH(CH₃)₂) | 4.7 g (17 mmol) | 1.7 | 2.6 | 2.1 | 69 |

(Note 1)
The quantitative analysis was conducted by subjecting a portion of the reaction mixture to high performance liquid chromatography.
(Note 2)
Shown is the yield of a mixture of prednisolone 21-(2E,6E-farnesylate) and prednisolone 21-(2Z,6E-farnesylate)(The molar ratio in every example was about 9 to 1.) as obtained by subjecting the concentrate of the filtrate of the reaction mixture to silica gel column chromatography.
(Note 3)
Shown is the yield of the isolated prednisolone 21-(2E,6E-farnesylate).
(Note 4)
Shown is the yield of the isolated prednisolone 21-(2E,6E-farnesylate) on the basis of the consumed prednisolone.

EXAMPLE 21

To a mixed solution of 56.72 g (240 mmol) of 2E,6E-farnesylic acid, 0.381 g (2.4 mmol) of 4-(dimethylamino)-pyridine hydrochloride and 100 ml of hexane, a solution of 26.00 g (126 mmol) of N,N'-dicyclohexylcarbodiimide and 100 ml of hexane was added dropwise while stirring under ice-cooling over a period of 9 hours. After the addition operation, the mixture was stirred at room temperature for further 12 hours. The obtained reaction mixture was filtered thereby to remove dicyclohexylurea. The filtrate was washed with water, 1% aqueous solution of sodium bicarbonate and water in this sequence and dried over anhydrous sodium sulfate. The residue obtained by distilling off the solvent was dissolved in 50 ml of tetrahydrofuran. The resulting solution was added dropwise to a mixture of 36.05 g (100 mmol) of prednisolone, 0.611 g (5.0 mmol) of 4-(dimethylamino)-pyridine and 50 ml of tetrahydrofuran over a period of 6 hours. After the addition, the

EXAMPLE 22

To a mixture of 66.08 g (280 mmol) of 2E,6E-farnesylic acid and 100 ml of methylene chloride was added a solution of 32.96 g (160 mmol) of N,N'-dicyclohexylcarbodiimide and 100 ml of methylene chloride while stirring under ice-cooling over a period of 9 hours. After the addition, the mixture was stirred at room temperature for further 12 hours. The resulting reaction mixture was filtered to remove dicyclohexylurea. The residue obtained by distilling off the solvent from the filtrate was dissolved in 50 ml of tetrahydrofuran. The resulting solution was added to a mixture of 36.05 g (100 mmol) of prednisolone, 0.611 g (5.0 mmol) of 4-(dimethylamino)pyridine and 50 ml of tetrahydrofuran and then stirred at room temperature for 3 days.

A portion of the reaction mixture thus obtained was analyzed by high performance liquid chromatography and as a result, it was found that the residual amount of prednisolone in the mixture was 0.14 g (0.4 mmol) and the yield of prednisolone 21-farnesylate was 56.9 g (98.4 mmol). The prednisolone 21-farnesylate was proved to be a mixture of prednisolone 21-(2E,6E-farnesylate) and prednisolone 21-(2Z,6E-farnesylate) (molar ratio: 93 to 7). To the residue obtained by distilling off the solvent from the reaction mixture was added 250 ml of ethyl acetate, and the residue was dissolved under heating and filtered while it remained heated. To the obtained filtrate, 500 ml of hexane was added dropwise at about 60° C. to 70° C. and after the termination of addition, gradually cooled down to room temperature. The precipitated crystal was separated by filtration followed by recrystallization from 160 ml of methanol. Prednisolone 21-(2E,6E-farnesylate), 32.04 g (55.4 mmol), was obtained as white crystals. The yield of the isolated prednisolone 21-(2E,6E-farnesylate) was 56% on the basis of the consumed prednisolone.

EXAMPLES 23 AND 24

The procedures of Example 22 for the reaction and separation-purification were repeated except that given amounts of carbodiimides as listed in Table 6 below were used in place of 32.96 g (160 mmol) of N,N'-dicyclohexylcarbodiimide, and prednisolone 21-(2E,6E-farnesylate) was obtained. The obtained results are shown in Table 6.

TABLE 6

| | Carbodiimides | | Yield of prednisolone 21-(2E,6E-farnesylate) |
|---|---|---|---|
| Example | Species | Amount | (%) (Note 1) |
| 23 | (CH$_3$)$_2$CH—N=C=N—CH(CH$_3$)$_2$ | 20.16 g (160 mmol) | 51 |
| 24 | C$_6$H$_5$—N=C=N—C$_2$H$_5$ | 23.36 g (160 mmol) | 49 |

(Note 1)
The yield of the isolated prednisolone 21-(2E,6E-farnesylate) on the basis of the consumed prednisolone.

EXAMPLE 25

To a mixed solution of 23.6 g (100 mmol) of 2E,6E-farnesylic acid, 0.159 g (1.0 mmol) of 4-(dimethylamino)-pyridine hydrochloride and 50 ml of tetrahydrofuran was added dropwise a solution containing 12.1 g (59 mmol) of N,N'-dicyclohexylcarbodiimide and 50 ml of tetrahydrofuran while stirring under ice-cooling for 10 minutes. After the addition, the mixture was stirred at room temperature for further 12 hours. The resulting reaction mixture was filtered thereby to remove dicyclohexylurea. The solvent was distilled off from the filtrate, and the obtained residue was subjected to silica gel column chromatography (developing solvent: a mixed solvent of ethyl acetate and hexane) to give 21.8 g (48 mmol) of 2E,6E-farnesylic anhydride having the following properties. FD-Mass spectrum: 454 (M$^+$)

$^1$H-NMR spectrum (90MHz) δTMS: 5.65 (s, 2H); 5.03 (m, 4H); 2.17 (s, 6H); 2.3–1.85 (m, 16H); 1.62 (s, 6H); 1.55 (s, 12H)

EXAMPLES 26–29

To a mixed solution of 23.6 g (100 mmol) of 2E,6E-farnesylic acid and 50 ml of a solvent shown in Table 7, a solution containing a given amount of N,N'-dicyclohexylcarbodiimide and 50 ml of tetrahydrofuran was added dropwise while stirring under ice-cooling over a period of 6 hours. After the addition, the mixture was stirred at room temperature for further 12 hours. The resulting reaction mixture was filtered thereby to remove dicyclohexyl urea. The solvent was distilled off from the filtrate, and the obtained residue was subjected to silica gel column chromatography (developing solvent: a mixed solvent of ethyl acetate and hexane) to give 2E,6E-farnesylic anhydride. The obtained results are shown in Table 7.

TABLE 7

| Example | Solvent | Amount of N,N'-dicyclohexyl-carbodiimide | Yield of 2E,6E-farnesylic anhydride |
|---|---|---|---|
| 26 | Hexane | 12.4 g (60 mmol) | 80% |
| 27 | Methylene chloride | 12.4 g (60 mmol) | 80% |
| 28 | Ethyl acetate | 13.4 g (65 mmol) | 64% |
| 29 | Tetrahydrofuran | 16.5 g (80 mmol) | 40% |

EXAMPLE 30

A mixture of 3.60 g (10.0 mmol) of prednisolone, 0.061 g (0.5 mmol) of 4-(dimethylamino)pyridine, 5.0 g (11 mmol) of 2E,6E-farnesylic anhydride and 15 ml of methylene chloride was stirred at room temperature for 3 days. A portion of the obtained reaction mixture was analyzed by high performance liquid chromatography and as a result, it was found that the residue amount of prednisolone in the mixture was 0.40 g (1.1 mmol) and the yield of prednisolone 21-farnesylate was proved to be 4.90 g (8.5 mmol). The prednisolone 21-farnesylate was a mixture of prednisolone 21-(2E,6E-farnesylate) and prednisolone 21-(2Z,6E-farnesylate)(molar ratio: 93 to 7). The solvent was distilled off from the reaction mixture and the resulting residue was subjected to silica gel column chromatography (developing solvent: a mixed solvent of ethyl acetate and hexane) to give 4.6 g (8.0 mmol) of prednisolone 21-farnesylate. The prednisolone 21-farnesylate was washed with diethyl ether to give 3.8 g (6.6 mmol) of prednisolone 21-(2E,6E-farnesylate) as a white solid. The yield of the isolated prednisolone 21-(2E,6E-farnesylate) was 74% on the basis of the consumed prednisolone.

EXAMPLE 31

A solution of 2.60 g (11.0 mmol) of 2E,6E-farnesylic acid, 2.72 g (11.0 mmol) of 1-ethoxycarbonyl-2-ethoxy-1,2-dihydroquinoline and 15 ml of methylene chloride was stirred at room temperature for 24 hours. To the resulting reaction mixture were added 3.60 g (10.0 mmol) of prednisolone and 0.061 g (0.5 mmol) of 4-(dimethylamino)pyridine, and then the whole mixture was stirred at room temperature for 3 days. The obtained reaction mixture was filtered, and the filtrate was washed with dilute hydrochloric acid, aqueous solution of sodium bicarbonate and water in this sequence and dried over anhydrous sodium sulfate. The solvent was distilled off, and the obtained residue was subjected to silica gel column chromatography (developing solvent: mixed solvent of ethyl acetate and hexane) to give 2.43 g (4.20 mmol) of prednisolone 21-farnesylate. A portion of the prednisolone 21-farnesylate thus obtained was analyzed by high performance liquid chromatography, from which it was found that the prednisolone 21-farnesylate was a mixture of prednisolone 21-(2E,6E-farnesylate) and prednisolone 21-(2Z,6E-farnesylate) (molar ratio: 92 to 8). This prednisolone 21-farnesylate was washed with diethyl ether to give 2.02 g (3.49 mmol) of prednisolone 21-(2E,6E-farnesylate) as a white solid. The yield of the isolated prednisolone 21-(2E,6E-farnesylate) was 35% on the basis of the consumed prednisolone.

EXAMPLE 32

| Tablets | |
| --- | --- |
| Prednisolone 21-(2E,6E-farnesylate) | 10 g |
| Corn starch | 65 g |
| Carboxycellulose | 20 g |
| Polyvinylpyrrolidone | 3 g |
| Calcium stearate | 2 g |
| Total amount | 100 g |

By the conventional method, prepared were 100 mg-tablets which contain 10 mg of prednisolone 21-(2E,6E-farnesylate) per tablet.

EXAMPLE 33

| Powders, capsules | |
| --- | --- |
| Prednisolone 21-(2E,6E-farnesylate) | 5 g |
| Crystalline cellulose | 95 g |
| Total amount | 100 g |

The composite powders were mixed and made into powders. Further, these powders were filled into No. 5 hard capsules to give capsules.

EXAMPLE 34

| Gel ointment | |
| --- | --- |
| Prednisolone 21-(2E,6E-farnesylate) | 1.6 g |
| Carboxyvinylpolymer (Product of Wako Pure Chemical Industries Ltd. HIVISWAKO-104) | 1.2 g |
| Hydroxypropylmethylcellulose 2910 (Product of Shin-Etsu Chemical Co., Ltd. Metolose 60SH-50) | 1.0 g |
| Macrogol 400 | 14.0 g |
| Macrogol 4000 | 1.0 g |
| Diethyl sebacate (product of Nikko Chemicals Co., Ltd. Nikkol DES-SP) | 5.0 g |
| Isopropyl alcohol | 48.0 g |
| Triisopropanolamine | 0.55 g |
| Purified water | 27.65 g |
| Total amount | 100.00 g |

Throughout 22.8 g of purified water was dispersed 1.2 g of carboxyvinylpolymer. To this dispersing liquid was added a dispersing liquid of 1.0 g of hydroxypropylmethyl cellulose 2910 in 24.0 g of isopropyl alcohol to give a mixture. Prednisolone 21-(2E,6E-farnesylate) (1.6 g) was dissolved in a mixture of 5.0 g of diethyl sebacate and 24.0 g of isopropyl alcohol to give a solution. The thus-obtained solution was mixed with the above-mentioned mixture. The obtained mixture was mixed with 14.0 g pf macrogol 400 and 1.0 g of macrogol 4000, and then mixed with a solution of 0.55 g triisopropanolamine in 0.55 g of purified water and also with 4.30 g of purified water.

EXAMPLE 35

| Water-miscible cream | |
| --- | --- |
| Prednisolone 21-(2E,6E-farnesylate) | 1.0% w/w |
| Bees wax (white) | 15.0% w/w |
| Cetostearyl alcohol BPC | 7.0% w/w |
| Cetomacrogol 1000BPC | 3.0% w/w |
| Liquid paraffin BP | 5.0% w/w |
| Chlorocresol | 0.1% w/w |
| Purified water | the amount to make the sum total amount to 100 weight parts |

Prednisolone 21-(2E,6E-farnesylate) and a small amount of liquid paraffin were subjected to ball mill treatment to be fined to such a particle size that 95% of the total particles were not more than 5μ. Water to be used was heated to 100° C., and chrolocresol was added thereto to be dissolved while stirring. The solution was cooled to 65° C. Bees wax, cetostearyl alcohol and cetomacrogol were fuged together, and the mixture was maintained at 65° C. The suspension of prednisolone 21-(2E,6E-farnesylate) was added thereto, and the mixture was rinsed with the use of the remaining liquid paraffin. The oily layer of prednisolone 21-(2E,6E-farnesylate) at 60° C. was added to the aqueous layer of chlorocresol at 65° C., and while stirring rapidly, this emulsion was cooled below the gelling-point (40-45° C.). The mixture was kept stirring at a low speed till the cream became solidified.

EXAMPLE 36

| Aerosol form | |
| --- | --- |
| Prednisolone 21-(2E,6E-farnesylate) | 0.05% |
| Ethanol | 10% |
| Lecithin | 0.2% |
| A mixture of dichlorodifluoromethane and dichlorotetrafluoroethane (70:30 mixture) | the amount to make the total amount to 100% |

The above-mentioned ingredients were mixed to make an aerosol.

REFERENCE EXAMPLE 1

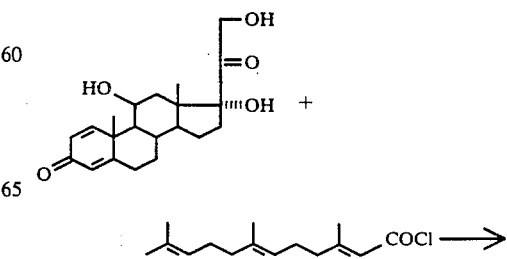

-continued

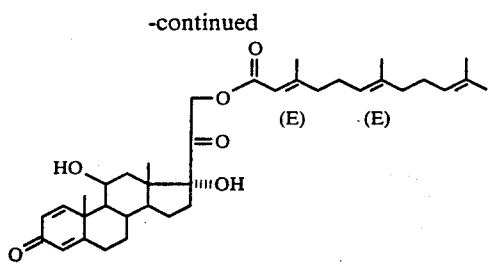

To a mixture of 20.0 g (55.5 mmol) of prednisolone, 6.0 g (75.8 mmol) of pyridine and 300 ml of tetrahydrofuran was added dropwise under ice-cooling 13.0 g (51.0 mmol) of a mixture of (E,E)-3,7,11-trimethyl-2,6,10-dodecatrienoyl chloride and (Z,E)-3,7,11-trimethyl-2,6,10-dodecatrienoyl chloride (molar ratio: about 6 to 4) and 10 ml of tetrahydrofuran. After the completion of the dropwise addition, the mixture was stirred under ice-cooling for 3 hours, and then stirred at room temperature overnight. The reaction mixture was poured into water and then extracted with ethyl acetate. The organic layer was washed with a saturated aqueous solution of ammonium chloride, a saturated aqueous solution of sodium bicarbonate and a saturated aqueous solution of sodium chloride in this sequence, and dried over anhydrous sodium sulfate. The residue, which was obtained by distilling off the compound of lower-boiling point, was subjected to silica gel column chromatography (developing solvent: a mixed solvent of ethyl acetate and hexane) to give 13.1 g of a mixture of prednisolone 21-(2E,6E-farnesylate) and prednisolone 21-(2Z,6E-farnesylate) as a white solid. This mixture was washed with 100 ml of diethyl ether to give 6.2 g (10.7 mmol) of prednisolne 21-(2E,6E-farnesylate) as white crystals having the following properties.

Yield: 19% (on the basis of the used prednisolone)
m.p. 152–154° C.
FD-Mass spectrum: 578 (M+)
$^1$H-NMR spectrum (500 MHz) $\delta_{TMS}^{CDCl_3}$: 7.29 (d, J=10Hz, 1H); 6.28 (d, J=10Hz, 1H); 6.02 (s, 1H); 5.81 (s, 1H); 5.10 (m, 2H); 5.05 (d, J=18Hz, 2H); 4.89 (d, J=18Hz, 1H); 4.49 (m, 1H); 2.17 (s, 3H); 1.70 (s, 3H); 1.63 (s,6H); 1.47 (s, 3H); 1.00 (s, 3H)
$^{13}$C-NMR spectrum (125MHz) $\delta^{CD_3OD}$: 206.4, 187.9, 173.6, 166.5, 161.4, 159.0, 136.3, 131.2, 126.8, 124.4, 123.2, 121.5, 115.1, 89.7, 69.9, 67.5, 56.4, 51.9, 45.1, 40.9, 39.8, 39.3, 34.6, 33.7, 32.2, 31.7, 26.8, 26.0, 24.9, 23.9, 20.63, 20.57, 18.1, 16.8, 16.3, 15.2

Next, there are shown examples of pharmaceutical preparations containing prednisolone 21-(2E,6E-farnesylate) of the present invention.

REFERENCE EXAMPLE 2

The diethyl ether solution which was obtained by washing in Reference Example 1 was concentrated under reduced pressure, and 6.9 g of the obtained concentrate was subjected to high performance liquid chromatography (column filler: silica gel; developing solvent: a mixed solvent of dichloromethane and dioxane) to give 1.0 g (1.7 mmol) of prednisolone 21-(2Z,6E-farnesylate) as viscous pale yellow liquid having the following properties.

Yield: 3% (on the basis of the used prednisolone)
FD-Mass spectrum: 578 (M+)
$^1$H-MNR spectrum (500 MHz) $\delta_{TMS}^{CDCl_3}$: 7.27 (d, J=10Hz, 1H); 6.28 (d, J=10Hz, 1H); 6.02 (s, 1H); 5.78 (s, 1H); 5.15 (m, 1H); 5.09 (m, 1H); 5.03 (d, J=18Hz, 1H); 4.87 (d, J=18Hz, 1H); 4.49 (m, 1H); 1.93 (s, 3H); 1.67 (s, 3H); 1.60 (s, 6H); 1.46 (s, 3H); 1.00 (s, 3H)

REFERENCE EXAMPLE 3

A mixture of 12.0 g (51.0 mmol) of (Z,Z)-3,7,11-trimethyl-2,6,10-dodecatrienoic acid, 6.7 g (56 mmol) of thionyl chloride and 100 ml of benzene was heated under reflux for 2 hours. The obtained reaction mixture was concentrated under reduced pressure to give 13.0 g (51.0 mmol) of the acid chloride. By conducting the reaction and the treatment of the reaction mixture in the same manner as in Reference Example 1 using 13.0 g (51.0 mmol) of the above-mentioned acid chloride in place of 13.0 g (51.0 mmol) of a mixture of (E,E)-3,7,11-trimethyl-2,6,10-dodecatrienoyl chloride and (Z,E)-3,7,11-trimethyl-2,6,10-dodecatrienoyl chloride, 11.5 g of a mixture of prednisolone 21-(2Z,6Z-farnesylate) and 11β,17α,21-trihydroxy-1,4-pregnadiene-3,20-dione 21[(E,Z)-3,7,11-trimethyl-2,6,10-dodecatrienoate] was obtained as a fraction by silica gel column chromatography. This mixture was subjected to high performance liquid chromatography (column filler: octadecylsillylated silica gel; developing solvent: a mixed solvent of methanol and water) to give 1.5 g (2.6 mmol) of prednisolone 21-(2Z,6Z-farnesylate) as viscous pale yellow liquid.

Yield 5% (on the basis of the used prednisolone)
FD-Mass spectrum: 578 (M+)
$^1$H-NMR spectrum (500 MHz) $\delta_{TMS}^{CDCl_3}$: 7.26 (d, J=10Hz, 1H); 6.27 (d, J=10Hz, 1H), 6.01 (s, 1H); 5.78 (s, 1H); 5.15 (m, 2H); 5.03 (d, J=18Hz, 1H); 4.86 (d, J=18Hz, 1H); 4.48 (m, 1H); 1.93 (s, 3H); 1.68 (s, 6H); 1.61 (s, 3H); 1.46 (s, 3H); 0.99 (s, 3H)

We claim:
1. A method for the production of 11β,17α,21-trihydroxy-1,4-pregnadiene-3,20-dione 21-[(E,E)-3,7,11-trimethyl-2,6,10-dodecatrienoate], which comprises reacting prednisolone and (E,E)-3,7,11-trimethyl-2,6,10-dodecatrienoic acid in the presence of (disubstituted amino)pyridines and a condensing agent.

* * * * *

UNITED STATES PATENT AND TRADEMARK OFFICE
CERTIFICATE OF CORRECTION

PATENT NO. : 5,015,746
DATED : May 14, 1991
INVENTOR(S) : Yutaka MIZUSHIMA et al.

It is certified that error appears in the above-identified patent and that said Letters Patent is hereby corrected as shown below:

On the Title page, item [54]

Correct the title to read METHOD FOR THE PRODUCTION OF $11\beta$, $17\alpha$, 21-TRIHYDROXY-1,4-PREGNADIENE-3,20-DIONE 21-[(E,E)-3,7,11-TRIMETHYL-2,6,10-DODECATRIENOATE].

In column 5, line 12, amend "(4-pyridyl)-guanidine" to "(4-pyridyl)guanidine".

In column 17, line 68, amend "(3-dimethylaminopropyl)-carbodiimide" to "(3-dimethylaminopropyl)carbodiimide".

In column 19, lines 52 to 53, amend "4-(dimethylamino)-pyridine" to "4-(dimethylamino)pyridine".

In column 22, line 5, amend "dicyclohexyl urea" to "dicyclohexylurea".

Signed and Sealed this

Nineteenth Day of October, 1993

Attest:

BRUCE LEHMAN

*Attesting Officer*     *Commissioner of Patents and Trademarks*